United States Patent [19]

Niizawa et al.

[11] Patent Number: 5,139,330
[45] Date of Patent: Aug. 18, 1992

[54] STANDARD SAMPLES AND METHODS OF INSTRUMENTAL MEASUREMENT OF ASTM COLOR OF PETROLEUM PRODUCTS USING SAID SAMPLES

[75] Inventors: Akihiko Niizawa; Masahiro Yamaguchi, both of Yokohama, Japan

[73] Assignees: Nippon Petroleum Refining Co., Ltd., Shimbashi; The Japan Petroleum Institute, Ikebukuro, both of Japan

[21] Appl. No.: 767,519

[22] Filed: Sep. 30, 1991

[30] Foreign Application Priority Data

Oct. 19, 1990 [JP] Japan .................... 2-279458

[51] Int. Cl.$^5$ .............................. G01N 33/28
[52] U.S. Cl. ............................. 356/70; 356/243
[58] Field of Search .................... 356/70, 243, 436

[56] References Cited

U.S. PATENT DOCUMENTS 3,951,854  4/1976  Sias et al. .................. 356/70 X

FOREIGN PATENT DOCUMENTS 0128633  12/1984  European Pat. Off. .
1584880   1/1970  France .
2457310   3/1980  France .

Primary Examiner—Vincent P. McGraw
Attorney, Agent, or Firm—Bucknam and Archer

[57] ABSTRACT

A standard sample for use in an instrumental measurement of ASTM color of a petroleum product with a photoelectric colorimeter, which comprises a mixed solution 3-methyl-1-phenyl-4-(phenylazo)-pyrazol-5-ol, 1-(phenylazo)-2-naphthalenol, 1-[[4-[(dimethylphenyl)azo]dimethylphenyl]azo]-2-naphthalenol, 1,5(or 1,8)-bis[(4-methylphenyl)amino]-9,10-anthracenedione, 1-hydroxy-4-[(4-methylphenyl)amino]-9,10-anthracenedione, 1,4-bis(butylamino)-9,10-anthracenedione and 1,4-bis[(4-butylphenyl)amino]-5,8-dihydroxy-9,10-anthracenedione each as a colorant, 1-phenyl-1-xylylethane as a solvent for said colorants and dodecane as a diluent, and a method of instrumental measurement of ASTM color with the standard sample.

4 Claims, 1 Drawing Sheet

STANDARD SAMPLES AND METHODS OF INSTRUMENTAL MEASUREMENT OF ASTM COLOR OF PETROLEUM PRODUCTS USING SAID SAMPLES

BACKGROUND OF THE INVENTION

1. Field of the Invention

The present invention relates to a standard sample used for instrumental measurement of ASTM color with a photoelectric colorimeter (color and color difference meter) which is a color testing method for petroleum products such as various lubricating oils, petrolatum and microcrystalline wax, and a method of instrumental measurement of ASTM color of a petroleum product using said sample.

2. Prior Art

There are two color testing methods for petroleum products, that is, the testing method for ASTM color and the testing method for Saybolt color which are prescribed in JIS K 2580.

Of these, the testing method for ASTM color is applied to various lubricating oils and petrolatum, etc., and specifies the color of a sample with a chromaticity value ranging from 0.5 (light) to 8.0 (dark) generally obtained by comparing the color of the sample under test with the color of a standard colored glass by the use of an ASTM chromometer. The standard colored glass used in the above method is prescribed in its dispersion by the luminous transmittance using the XYZ colorimetric system and the CIE standard illuminants C and the chromaticity coordinates based on the RGB color system in accordance with JIS Z 8722.

However, in cases where the ASTM color is measured by the use of the ASTM chromometer, since the ASTM color is visually judged by a measurer and the specification of the measurement results is not quantitative (when the sample color is between those of two standard glasses, a symbol L is attached to the value of the standard glass having a darker color, while when the sample color is darker than 8.0, a value of D 8.0 is assigned thereto), the current situation is that a personal difference is apt to arise, bothering the measure in the judgement. This tendency is particularly remarkable when the sample color is dense or dark.

Under such circumstances, automatization of the color testing method without resort to visual measurement is eagerly desired at the present time.

In view of the above, an attempt was made by the present inventors to investigate whether or not a commercially available photoelectric colorimeter (measuring instrument) can be used for measuring the ASTM color.

A photoelectric colorimeter used must be one in which a favorable correlation with the testing method as prescribed in JIS K 2580 can be obtained in the entire range of ASTM color ranging from 0.5 to 8.0. Furthermore, a universal method of testing the color of material, especially that of liquid is desired.

In the perception of color with human eyes under natural light, the quantity of stimulus due to three primary colors including red, green and blue is an important factor. In measuring a color with an optical instrument, natural light is used as the light source and the quantity of stimulus is tristimulus values.

Accordingly as a testing method for ASTM color, a universal method close to the perception of color with human eyes based on the tristimulus values by an optical instrument is desirable, and also as a method of specifying the results of measurement, a quantitative specification system without the use of L or D color specification is desired. Therefore, the testing method based on the measuring methods for color of reflecting or transmitting objects recommended by Commission Internationale de l'Eclairage (hereinafter abbreviated to "CIE") and prescribed in JIS Z 8722 and also the quantitative specification method for measured results based on the color-specification method based on the X YZ color system as prescribed in JIS Z 8701 are desired.

In measuring the chromaticity with a photoelectric colorimeter, it is necessary to express the measured value of a sample obtained with a commercially available photoelectric colorimeter in terms of the ASTM color.

Therefore, it is necessary to obtain the correlation between the above two factors.

The result of comparison between the sum of optical densities ($\Sigma D$) based on the XYZ color system of a standard glass and the ASTM color of the same led to the finding of a correlation as represented by the following relationship formula:

$$A = \alpha \Sigma D + \beta$$

wherein A is ASTM color, $\Sigma D$ is sum of optical densities (DX+DY+DZ), and $\alpha$ and $\beta$ are each a constant for calibration of instrumental error.

Therefore, the measured value of the ASTM color is obtained by processing the measured X, Y and Z values in the operation-display section of the measuring instrument on the basis of the relationship formula.

As the above $\Sigma D$ value varies with an instrumental error depending on an instrument used, it cannot always be constant even for the same sample. It is necessary, therefore, to prepare a standard liquid sample for each ASTM color to calibrate each instrument (photoelectric colorimeter) therewith.

Such a standard sample is required to comprise a base material having a low volatility, resistance to oxidation, low deterioration, such as oxidation, with the elapse of time and good color stability.

SUMMARY OF THE INVENTION

It is an object of the present invention to provide a standard sample to be used for measuring ASTM color by the use of a photoelectric colorimeter (color and color difference meter) and an instrumental measuring method using said sample on the basis of the above-mentioned viewpoint.

In attempts to achieve the above object, the present inventors made intensive stydies and found that a colorants mixture (dyestuffs mixture) which meets such a requirement and is dissolved in a specific solvent coincides with a standard colored glass to be used in ASTM colorimetry in regard to the hue and exhibits a sufficient availability as a standard sample.

The standard sample of the present invention comprises a mixed solution comprising 3-methyl-1-phenyl-4-(phenylazo)-pyrazol-5-ol, 1-(phenylazo)-2-naphthalenol, 1-[[4-[(dimethylphenyl)azo]dimethylphenyl]azo]-2-naphthalenol, 1,5(or 1,8)-bis[(4-methylphenyl)amino]-9,10-anthracenedione, 1-hydroxy-4-[(4-methylphenyl)amino]-9,10-anthracenedione, 1,4-bis(butylamino)-9,10-anthracenedione and 1,4-bis[(4-butylphenyl)amino]-5,8-dihydroxy-9,10-anthracenedione each as a colorant, 1-phenyl-1-xylylethane as a solvent for said colorants and dodecane as a diluent.

This invention will be explained hereunder in more detail.

Each of the colorants to be used in the present invention has the following chemical structure:

(1) 3-methyl-1-phenyl-4-(phenylazo)-pyrazol-5-ol

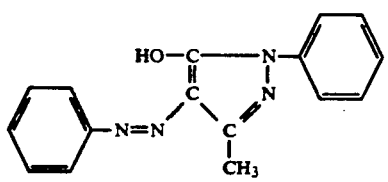

(CAS No. 4314-14-1)
Color index (CI): Solvent Yellow 16
Example: Oil Yellow 5GS Extra (tradename)

(2) 1-(phenylazo)-2-naphthalenol

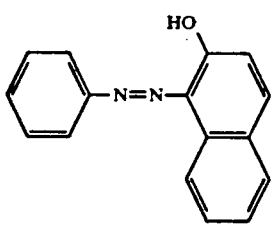

(CAS No. 842-07-9)
Color index (CI): Solvent Yellow 14
Example: Oil Orange Extra (tradename)

(3) 1-[[4-[(dimethylphenyl)azo]dimethylphenyl]azo]-2-naphthalenol

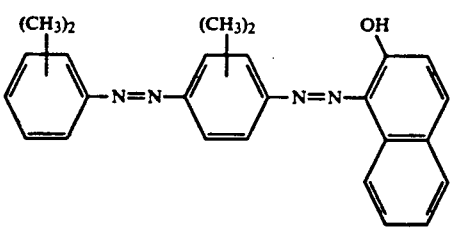

(CAS No. 1320-06-5)
Color index (CI): Solvent Red 27
Example: Oil Red 5B Special (tradename)

(4) 1,5(or 1,8)-bis[(4-methylphenyl)amino]-9,10-anthracenedione

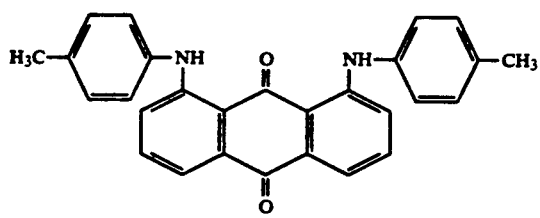

-continued

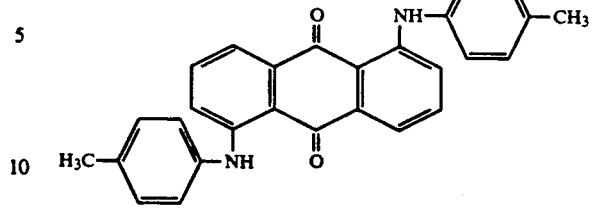

(CAS No. 8005-40-1)
Color index (CI): Solvent Violet 14
Example: Oil Violet 3R (tradename)

(5) 1-hydroxy-4-[(4-methylphenyl)amino]-9,10-anthracenedione

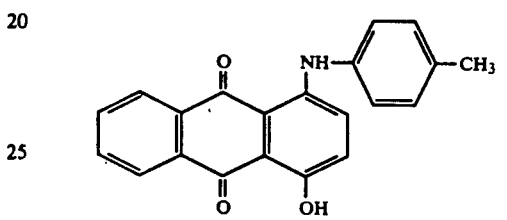

(CAS No. 81-48-1)
Color index (CI): Solvent Violet 13
Example: Oil Violet B-2R (tradename)

(6) 1,4-bis(butylamino)-9,10-anthracenedione

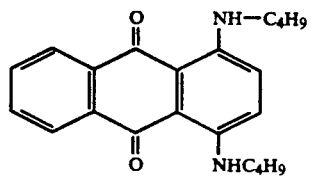

(CAS No. 17354-14-2)
Color index (CI): Solvent Blue 35
Example: Oil Blue SB (tradename)

(7) 1,4-bis[(4-butylphenyl)amino]-5,8-dihydroxy-9,10-anthracenedione

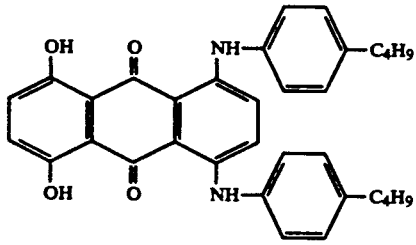

(CAS No. 28198-05-2)
Color index (CI): Solvent Green 28
Example: Oil Green SG (tradename)

The above-mentioned seven colorants are most preferably mixed at a ratio by volume of (1):(2):(3):(4):(5):(6):(7) of 183:55:13:11:16:1:3.

In a standard sample of the present invention, 1-phenyl-1-xylylethane (hereinafter abbreviated to "PXE") and dodecane (hereinafter referred to as "n-$C_{12}$") are used as a solvent for the colorants and as a diluent, respectively.

With regard to the preparation of a specific standard sample, each of the colorants (dyestuffs) is dissolved in PXE solvent to form 1,000 ppm (wt/vol %) of a dilute solution, the obtained dilute solutions are mixed together at the above ratio, and then the mixed solution is diluted with n-$C_{12}$ prescribed times, for example, 2 to 350 times to be uesd as a standard sample.

In the following, the instrumental measuring method of the present invention will be described.

If ASTM color measured with the above-mentioned photoelectric colorimeter for a standard sample (having a true ASTM color of 7.0) on the basis of the sum of optical densities ($\Sigma D$) of said sample and a predetermined relationship formula is 6.98, the ASTM color thus measured is adjusted to 7.0 by the operation of the correction key at the operation-display section to calibrate the meter.

By carrying out the calibration (correction) of the meter with the use of the standard samples each having a true ASTM color from each other in the range of 0.5 to 8.0 in the same manner as above, the correct use of the photoelectric colorimeter is made possible.

As described hereinbefore, the instrumental measurement of the ASTM color of a petroleum product can be carried out quantitatively and accurately by the use of the standard sample of the present invention.

DESCRIPTION OF THE PREFERRED EMBODIMENTS

Figure 1:
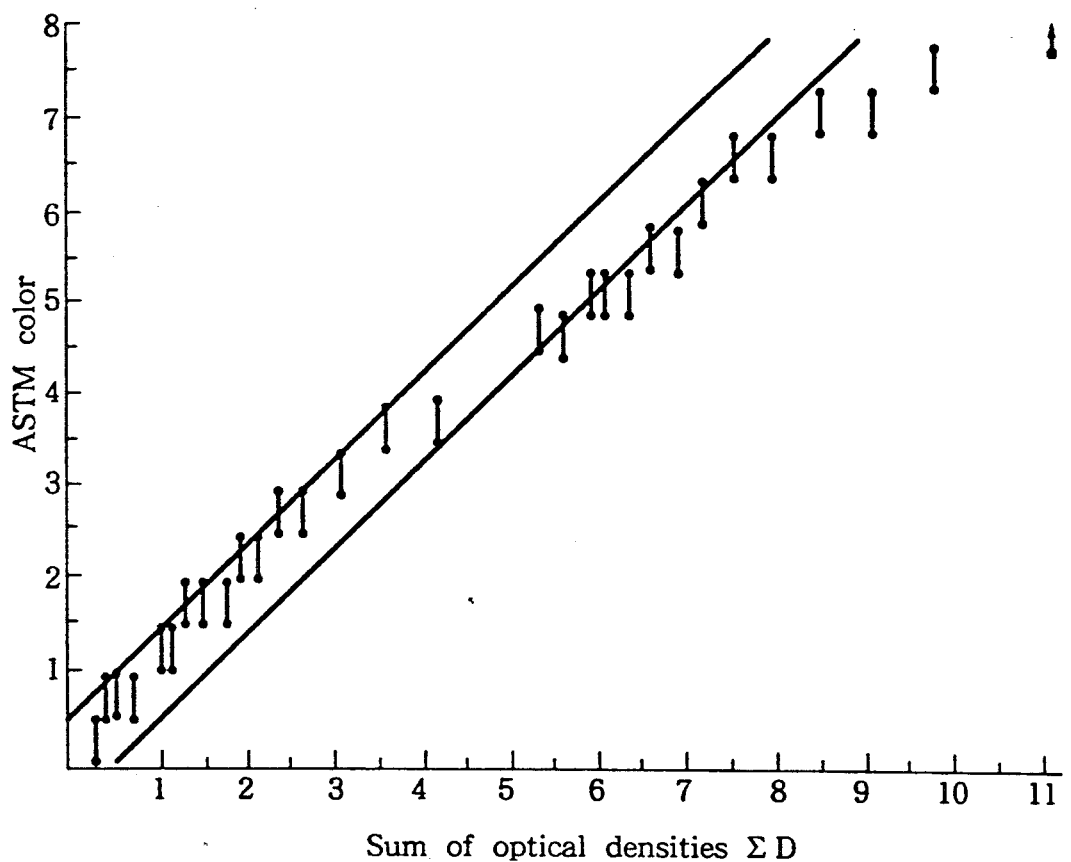
FIG. 1 is a graph showing the relation between $\Sigma D$ and ASTM color.

The present invention will now be described in more detail by referring to the following Example.

EXAMPLE

Each of 31 standard samples was prepared by dissolving each of 3-methyl-1-phenyl-4-(phenylazo)-pyrazol-5-ol,1-(phenylazo)-2-naphthalenol, 1-[[4-[(dimethylphenyl)azo]dimethylphenyl]azo]-2-naphthalenol, 1,5(or 1,8)-bis [(4-methylphenyl)amino]-9,10-anthracenedione, 1-hydroxy-4-[(4-methylphenyl)amino]-9, 10-anthracenedione, 1,4-bis(butylamino)-9,10-anthracenedione and 1,4-bis[(4-butylphenyl)amino]-5,8-dihydroxy-9,10-anthracenedione in PXE solvent (1-phenyl-1-xylylethane) to obtain 1000ppm(Wt/vol %) of a dilute solution, mixing the obtained dilute solutions in a ratio by volume of 183:53:13:11:16:1:3, and then diluting the mixed colorants solution with n-$C_{12}$ with a dilution as specified in Table 1. The sum of optical densities ($\Sigma D$) of each of said samples was measured by the use of a photoelectric colorimeter (Chroma meter CT-210 custom, produced by Minolta Camera Co., Ltd.) in which a sampling cell having a cell length of 33 mm and a CIE standard source C were employed.

Further, the ASTM color of each of said standard samples was measured by the use of a conventional ASTM chromometer and by 4 measurers (A–D), respectively.

The results are shown in Table 1 and FIG. 1.

TABLE 1

| Standard sample No. | Dilution | ASTM color Measurer A | Measurer B | Measurer C | Measurer D | Sum of optical densities $\Sigma D$ |
|---|---|---|---|---|---|---|
| 1 | 2 | D 8.0 | D 8.0 | D 8.0 | D 8.0 | 10.7 |
| 2 | 3 | L 8.0 | L 8.0 | L 8.0 | L 8.0 | 9.4 |
| 3 | 4 | L 8.0 | L 8.0 | L 8.0 | 7.5 | 8.7 |
| 4 | 5 | L 7.5 | L 7.5 | L 7.5 | L 7.5 | 8.1 |
| 5 | 6 | L 7.0 | 7.0 | L 7.0 | L 7.0 | 7.6 |
| 6 | 7 | L 7.0 | L 7.0 | L 7.0 | L 7.0 | 7.2 |
| 7 | 8 | 6.5 | L 6.5 | L 6.5 | L 6.5 | 6.9 |
| 8 | 9 | L 6.0 | L 6.0 | L 6.0 | 6.0 | 6.6 |
| 9 | 10 | L 6.0 | L 6.0 | L 6.0 | L 6.0 | 6.3 |
| 10 | 11 | L 5.5 | L 5.5 | 5.5 | L 5.5 | 6.1 |
| 11 | 12 | L 5.5 | L 5.5 | L 5.5 | L 5.5 | 5.8 |
| 12 | 13 | L 5.5 | L 5.5 | L 5.5 | L 5.5 | 5.7 |
| 13 | 14 | L 5.0 | 5.0 | L 5.0 | L 5.0 | 5.4 |
| 14 | 15 | L 5.0 | L 5.0 | L 5.0 | L 5.0 | 5.1 |
| 15 | 20 | L 4.0 | L 4.0 | L 4.0 | 4.0 | 4.0 |
| 16 | 25 | L 4.0 | L 4.0 | L 4.0 | L 4.0 | 3.4 |
| 17 | 30 | L 3.5 | L 3.5 | L 3.5 | L 3.5 | 2.9 |
| 18 | 35 | L 3.0 | L 3.0 | L 3.0 | 3.0 | 2.5 |
| 19 | 40 | L 3.0 | L 3.0 | L 3.0 | L 3.0 | 2.2 |
| 20 | 45 | 2.5 | L 2.5 | L 2.5 | L 2.5 | 2.0 |
| 21 | 50 | L 2.5 | L 2.5 | L 2.5 | L 2.5 | 1.8 |
| 22 | 60 | L 2.0 | 2.0 | L 2.0 | L 2.0 | 1.7 |
| 23 | 70 | L 2.0 | L 2.0 | L 2.0 | L 2.0 | 1.4 |
| 24 | 80 | L 2.0 | L 2.0 | L 2.0 | L 2.0 | 1.2 |
| 25 | 90 | L 1.5 | L 1.5 | L 1.5 | L 1.5 | 1.1 |
| 26 | 100 | L 1.5 | L 1.5 | L 1.5 | L 1.5 | 1.0 |
| 27 | 150 | L 1.0 | L 1.0 | L 1.0 | L 1.0 | 0.7 |
| 28 | 200 | L 1.0 | L 1.0 | L 1.0 | L 1.0 | 0.5 |
| 29 | 250 | L 1.0 | L 1.0 | L 1.0 | L 1.0 | 0.4 |
| 30 | 300 | 0.5 | 0.5 | L 0.5 | 0.5 | 0.3 |
| 31 | 350 | L 0.5 | L 0.5 | L 0.5 | L 0.5 | 0.3 |

As can be seen from Table 1 and FIG. 1, the $\Sigma D$ value of each of the standard samples corresponds appropriately to each ASTM color. Furthermore, the reproduction error of the $\Sigma D$ value was favorably small.

What is claimed is:

1. A standard sample for use in an instrumental measurement of ASTM color of a petroleum product with a photoelectric colorimeter, which comprises a mixed solution of 3-methyl-1-phenyl-4-(phenylazo)-pyrazol-5-ol, 1-(phenylazo)-2-naphthalenol, 1-[[4-[(dimethylphenyl)azo]dimethylphenyl]azo]-2-naphthalenol, 1,5(or 1,8)-bis[(4-methylphenyl)amino]-9,10-anthracenedione, 1-hydroxy-4-[(4-methylphenyl)amino]-9,10-anthracenedione, 1,4-bis(butylamino)-9,10-anthracenedione and 1,4-bis[(4-butylphenyl)amino]-5,8-dihydroxy-9,10-anthracenedione each as a colorant, 1-phenyl-1-xylylethane as a solvent for said colorants and dodecane as a diluent.

2. The standard sample according to claim 1, wherein said colorants 3-methyl-1-phenyl-4-(phenylazo)-pyrazol-5-ol, 1-(phenylazo)-2-naphthalenol, 1-[[4-[(dimethylphenyl)azo]dimethylphenyl]azo]-2-naphthalenol, 1,5(or 1,8)-bis[(4-methylphenyl)amino]-9,10-anthracenedione, 1-hydroxy-4-[(4-methylphenyl)amino]-9,10-anthracenedione, 1,4-bis(butylamino)-9,10-anthracenedione and 1,4-bis[(4-butylphenyl)amino]-5,8-dihydroxy-9,10-anthracenedione are compounded at a ratio by volume of 183:53:13:11:16:1:3.

3. A method of instrumental measurement of ASTM color of a petroleum product with a photoelectric colorimenter, which comprises calibrating the photoelectric colorimeter by the use of a standard sample comprising a mixed solution of 3-methyl-1-phenyl-4-(phenylazo)-pyrazol-5-ol, 1-(phenylazo)-2-naphthalenol, 1-[[4-[(dimethylphenyl)azo]dimethylphenyl- ]azo]-2-naphthalenol, 1,5(or 1,8)-bis[(4-methylphenyl)amino]-9,10-anthracenedione, 1-hydroxy-4-[(4-methylphenyl)amino]-9,10-anthracenedione, 1,4-bis(butylamino)-9,10-anthracenedione and 1,4-bis[(4-butylphenyl)amino]-5,8-dihydroxy-9,10-anthracenedione each as a colorant, 1-phenyl-1-xylylethane as a solvent for said colorants and dodecane as a diluent.

4. The method according to claim 3, wherein said colorants 3-methyl-1-phenyl-4-(phenylazo)-pyrazol-5-ol, 1-(phenylazo)-2-naphthalenol, 1-[[4-[(dimethylphenyl)azo]dimethylphenyl]azo]-2-naphthalenol, 1,5(or 1,8)-bis[(4-methylphenyl)amino]-9,10-anthracenedione, 1-hydroxy-4-[(4-methylphenyl)amino]-9,10-anthracenedione, 1,4-bis(butylamino)-9,10-anthracenedione and 1,4-bis[(4-butylphenyl)amino]-5,8-dihydroxy-9,10-anthracenedione are compounded at a ratio by volume of 183:53:13:11:16:1:3.

* * * * *